(12) United States Patent
Kwapil et al.

(10) Patent No.: US 7,689,270 B2
(45) Date of Patent: Mar. 30, 2010

(54) PHYSIOLOGICAL SENSOR SYSTEM FOR USE IN A MAGNETIC RESONANCE DEVICE

(75) Inventors: Gernot Kwapil, Neunkirchen (DE); Ulrich Schätzle, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 518 days.

(21) Appl. No.: 11/632,866

(22) PCT Filed: Jul. 22, 2005

(86) PCT No.: PCT/EP2005/053567

§ 371 (c)(1), (2), (4) Date: Jan. 19, 2007

(87) PCT Pub. No.: WO2006/015938

PCT Pub. Date: Feb. 16, 2006

(65) Prior Publication Data

US 2008/0012568 A1    Jan. 17, 2008

(30) Foreign Application Priority Data

Aug. 2, 2004  (DE) ................. 10 2004 037 375

(51) Int. Cl.
    *A61B 5/04*   (2006.01)
(52) U.S. Cl. .............. 600/509; 128/901; 600/411
(58) Field of Classification Search .............. 128/901; 324/322; 600/412, 372, 411, 509; 607/5, 607/2, 36, 40
See application file for complete search history.

(56) References Cited

U.S. PATENT DOCUMENTS 4,763,075 A    8/1988  Weigert
4,951,672 A *  8/1990  Buchwald et al. ............ 600/421
5,209,233 A *  5/1993  Holland et al. ............... 600/412

(Continued)

FOREIGN PATENT DOCUMENTS

DE    33 27 731 A1    2/1985

(Continued)

OTHER PUBLICATIONS

Louis Lemieux, Philip J. Allen, Florence Franconi, Mark R. Symms, David R. Fish, Recording of EEG During fMRI Experiments: Patient Safety:, Magnetic Resonance in Medicine, Dec. 1997, pp. 943-952, vol. 38, No. 6, XP000729808, ISSN: 0740-3194, Academic Press, Duluth, MN, US.

*Primary Examiner*—Carl H Layno
*Assistant Examiner*—Pamela M Bays

(57) ABSTRACT

The invention relates to a physiological sensor system for recording electric measuring signals in a magnetic resonance device, comprising at least one measuring electrode, a signal amplifier unit in a shielded housing that is placed in close proximity to a patient and a signal processing unit for preparing the measuring signals. According to the invention, the measuring electrode is connected to the signal amplifier unit via a cable connection. The invention is characterized in that the cable connection comprises a low-ohm conductor, which is connected to the measuring electrode by means of a first electric resistor on a first end and to the signal amplifier unit by means of a resistance between the skin and the measuring electrode. The development of heat caused by an induced current is concentrated on the resistors, so that there is no risk of burning to the patient.

13 Claims, 4 Drawing Sheets

U.S. PATENT DOCUMENTS

| | | | |
|---|---|---|---|
| 5,411,527 A * | 5/1995 | Alt | 607/5 |
| 5,691,641 A | 11/1997 | Cansell et al. | |
| 5,782,241 A | 7/1998 | Felblinger et al. | |
| 6,032,063 A * | 2/2000 | Hoar et al. | 600/372 |
| 6,044,294 A * | 3/2000 | Mortazavi et al. | 600/547 |
| 6,052,614 A | 4/2000 | Morris, Sr. et al. | |
| 6,711,434 B2 | 3/2004 | Kramer et al. | |

FOREIGN PATENT DOCUMENTS

| | | |
|---|---|---|
| DE | 34 30 625 A1 | 2/1986 |
| DE | 86 03 542 U1 | 7/1986 |
| DE | 696 28 354 T2 | 7/1996 |
| DE | 100 47 365 A1 | 5/2002 |
| EP | 0 132 785 A2 | 2/1985 |
| EP | 0 173 130 A1 | 3/1986 |

\* cited by examiner

PHYSIOLOGICAL SENSOR SYSTEM FOR USE IN A MAGNETIC RESONANCE DEVICE

CROSS REFERENCE TO RELATED APPLICATIONS

This application is the U.S. National Stage of International Application No. PCT/EP2005/053567 filed Jul. 22, 2005 and claims the benefits thereof. The International Application claims the benefits of German application No. 10 2004 037 375.2 filed Aug. 2, 2004, both of the applications are incorporated by reference herein in their entirety.

FIELD OF THE INVENTION

The invention relates to a physiological sensor system for recording electrical measurement signals in a magnetic resonance device.

BACKGROUND OF THE INVENTION

A physiological sensor system of this type is used for the in situ recording of physiological measurement signals during an examination of a patient using a magnetic resonance device (MR device). From the measurement signals can be obtained, for example, ECG derivatives which provide information about the heart phase during the examination and permit a synchronization of MR measurement sequences and the heart activity.

Thus, as a result of continuously sensing the position of the heart it is possible to control the image recording operation of the MR device. If the magnetic resonance images should show the heart in a particular valve position for example, then it is possible by using the ECG signals to sense exactly the moment at which the heart is in the desired valve position and to synchronize the image recording by this means, in other words to trigger the recording for example.

A physiological sensor system for recording electrical measurement signals in an environment which adversely affects the recording, in particular in a magnetic resonance device, is known from DE 100 47 365 A1. It has a plurality of measuring electrodes and also a signal amplifier unit, a power supply unit and an electronics facility for signal conversion and signal transfer to an external signal processing device and/or control device, whereby the measuring electrodes and the signal amplifier unit are arranged in a first shielded housing and the power supply unit and the electronics facility are arranged in a second shielded housing. In addition, the signal amplifier unit is or can be connected to the electronics facility and the power supply unit by way of a shielded and/or twisted cable connection.

Similar physiological sensor systems are known from U.S. Pat. No. 5,782,241 and U.S. Pat. No. 6,052,614, in which all the elements relevant to the recording and preprocessing operation of the measurement signals are arranged together in a single housing which is to be placed on the patient. However, from this configuration results the disadvantage that on account of the considerable structural size and the simultaneous integration of the measuring electrodes the sensor system needs to be positioned close to the heart. The danger thus exists that this sensor system is at least partially situated in the recording area, in other words in the area in which the magnetic resonance image is to be recorded. The latter is at least adversely affected as a result.

A facility for MR tomography is known from EP 0 173 130 A1, in which the electrodes are connected by way of a cable connection with an amplifier facility situated outside the MR device. From this amplifier facility, which is arranged together with the MR device in an HF chamber, the measurement signals are sent by way of a fiber-optic connection to a processing facility situated externally with respect to the chamber.

Further facilities for acquiring ECG signals, in particular also with regard to core-spin tomography, are known from DE 696 28 354 T2, DE 34 30 625 A1 and DE 33 27 731 A1. Cable connections between body electrodes and amplifiers which contain a safety resistor are Cable connections between body electrodes and amplifiers which contain a safety resistor are set down in the publications.

In general, the electrical and magnetic fields underlying the MR measurement sequences couple into electrical conductors. Also affected here are the cable connections with the electrodes for the measurement of the ECG derivatives for example, with the result that particularly in the case of an elevated basic magnetic field strength (for example, greater than 1 T) a reliable determination of the heart phase is adversely affected if no countermeasures are undertaken. In addition, the arrangement of measuring electrode and cable connection must be designed such that an inadmissible warming of the parts coming into contact with a patient caused by the fields to be coupled in is prevented. A further requirement relating to the physiological sensor system lies in the use of non-permeable materials since otherwise disturbance to the magnetic resonance images would occur. This causes difficulties particularly with regard to the implementation of the electrode clips. These are normally used in order to establish electrical contact with single-use adhesive electrodes by using a clamping contact. Their spring effect cannot be achieved using conventional springs made of magnetic materials.

MR measurement sequences comprise high-frequency signals, which are beamed into the imaging area of the MR device in order to generate MR response signals, and also gradient fields for location coding of the frequencies and phases of the MR response signals. Currents induced by the HF signals can flow from the measuring electrode to the patient, whereby a localized warming effect can occur as a result of the resistance between measuring electrode and skin in the order of magnitude of 10 k$\Omega$, which it is necessary to limit. This is achieved for example by means of a resistive line in the cable connection which limits the line currents and whereby the heat loss occurring is dissipated by being distributed over the entire line length. Carbon and stainless steel lines are known as resistive, non-permeable lines. Carbon lines consist of elastomers which are mixed with fine carbon and thereby become conducting. By adjusting the carbon proportion, the desired resistance value can be set in the order of magnitude of 10 kOhm/m. Stainless steel lines consist of extremely thin stainless steel wire which is wound onto a non-conducting carrier wire. The desired resistance value is on the other hand obtained as a result of the great line length achieved. Stainless steel lines are additionally very good at blocking the coupling-in of the electrical HF fields through the inductance formed by the winding. However, this also means that an increasing number of magnetic disturbances are captured as a result of the gradient fields. By contrast, carbon lines are less sensitive to magnetic disturbances. They are however more sensitive to high-frequency electrical disturbances. Since HF disturbances can be removed very well from the low-frequency ECG useful signal by means of low-pass filters, the carbon lines have the advantage over stainless steel lines. However, in the case of material transitions from a carbon line to the amplifier electronics or to the electrode clip there is a danger of a non-linear contact which results in a partial detection of the HF disturbance. These pass unhindered through the low-pass filters as an envelope curve signal and are amplified together with the ECG signal. This effect has also been observed with stainless steel lines which are manufactured using electrode clips made from carbon duroplast. Depending on the production quality of the material transitions, the level of the disturbance coupling-in can be a multiple of the QRS amplitude in the ECG signal, with the result that it becomes necessary to single out the lines of inferior quality. In addition, this disadvantageous effect can also be intensified during the course of use, with the result that the period of usability is restricted.

SUMMARY OF THE INVENTION

The object of the invention is to set down a cable connection from a measuring electrode to a signal amplifier unit for a physiological sensor system, whose interaction with the electromagnetic fields of the magnetic resonance device does not lead to a warming of the parts coming into contact with a patient and which does not exhibit the previously mentioned disadvantage of carbon/metal transitions, for example.

This object is achieved with reference to the physiological sensor system mentioned in the introduction by the fact that the cable connection has a low-impedance conductor which is connected by way of a first electrical resistor at a first end with the measuring electrode and by means of a second electrical resistor at a second end with the signal amplifier unit, whereby the resistors have a resistance value at least in the order of magnitude of the electrical resistance between skin and measuring electrode.

The invention permits the use of low-cost low-impedance conductors, copper braids for example, for connecting the measuring electrodes with the signal amplifier unit. Induced currents essentially cause waste heat at the resistors, which can be kept away from the patient as a result of the arrangement of the resistors. By preference, the low-impedance conductor is soldered together with the resistors, with the result that the problem of interference coupling-in is not present on account of the lack of electrical transitions.

Embodiments of the invention allow problem-free generation of ECG signals both at elevated basic magnetic field strengths (greater than 1 T) and also in the case of high-power sequences, in other words at elevated HF and gradient powers. The use of the facilities mentioned in the introduction for obtaining ECG signals does not allow this without problems.

As a result of the increase in the magnetic field strength, HF and gradient power in magnetic resonance technology, it is not possible to guarantee any applications which are free of interference and possible danger using the facilities mentioned in the introduction. The current upper limit for commercially used magnetic resonance devices presently lies at 3 T, whereby magnetic resonance devices with higher magnetic field strengths (7 T for example) are also undergoing clinical trials. These involve resonant frequencies of between 120 MHz and 280 MHz. Under these general conditions, cable insulations act as dielectric current conductors at high frequencies. Even relatively short lines become amazingly effective antennas which draw energy from the HF field and can deliver this as current to the ECG electrodes on the patient. The shielded housings can be heated by eddy currents. Serious consequences for the patient are for example burns in the areas where conductors are applied. Precautionary measures should be taken to prevent this. Furthermore, it is possible that required ECG-triggered magnetic resonance examinations may be performed incorrectly or may not be capable of being performed. Particularly with regard to the arrangements with only one resistor mentioned in the introduction, the problem arises that the current in the ECG derivative is limited at only one point by the resistor. The path length to the other end of the conductor does however again couple in sufficient energy at high frequencies ($\geq 120$ MHz) in order to induce HF voltages. In spite of insulation of the lines and housings, capacitively coupled currents flow over the body of the patient and endanger the latter. As a result of the inventive use of two resistors at the opposite ends, the effective path length is halved and the current is limited at the particularly critical points. This division of the series resistance into two spatially separated resistors takes account of the situation and the requirements of modern, for example cardio MR examinations and is thus of great benefit.

In a special embodiment, at least two measuring electrodes are used, whereby each of the cable connections is connected in such a way with the signal amplifier unit that the end of the second resistor is routed on the side of the signal amplifier unit with a feedthrough capacitor into the shielded housing and is thus connected HF-wise to the shielded housing. The use of two measuring electrodes with cable connections and of the HF-wise short-circuiting of the two cable connections by way of the shielded housing and also by way of the skin of the patient results in an HF-antenna-like design of conducting connections within the imaging area of the MR device. The inventive use of the resistors prevents a danger of burning for the patient in spite of the major coupling-in of HF signal power into this arrangement.

In a further embodiment, the connection of the second resistor to the measuring electrode is made by way of a clip which has a recess in which the first resistor is located. The resistor is preferably arranged on the side facing away from the patient, such that there is no or only a slight heat coupling from the resistor to the patient. The electrical connection between the first resistor and the measuring electrode is preferably effected by way of a tin-plating of a clamping zone of the clip and of the area between the clamping zone and a soldering zone on the first resistor.

Further advantageous embodiments of the invention are characterized by the features described in the subclaims.

BRIEF DESCRIPTION OF THE DRAWINGS

A plurality of embodiments of the invention will be described in the following with reference to FIGS. 1 to 3. In the drawings.

DETAILED DESCRIPTION OF THE INVENTION

Figure 1:
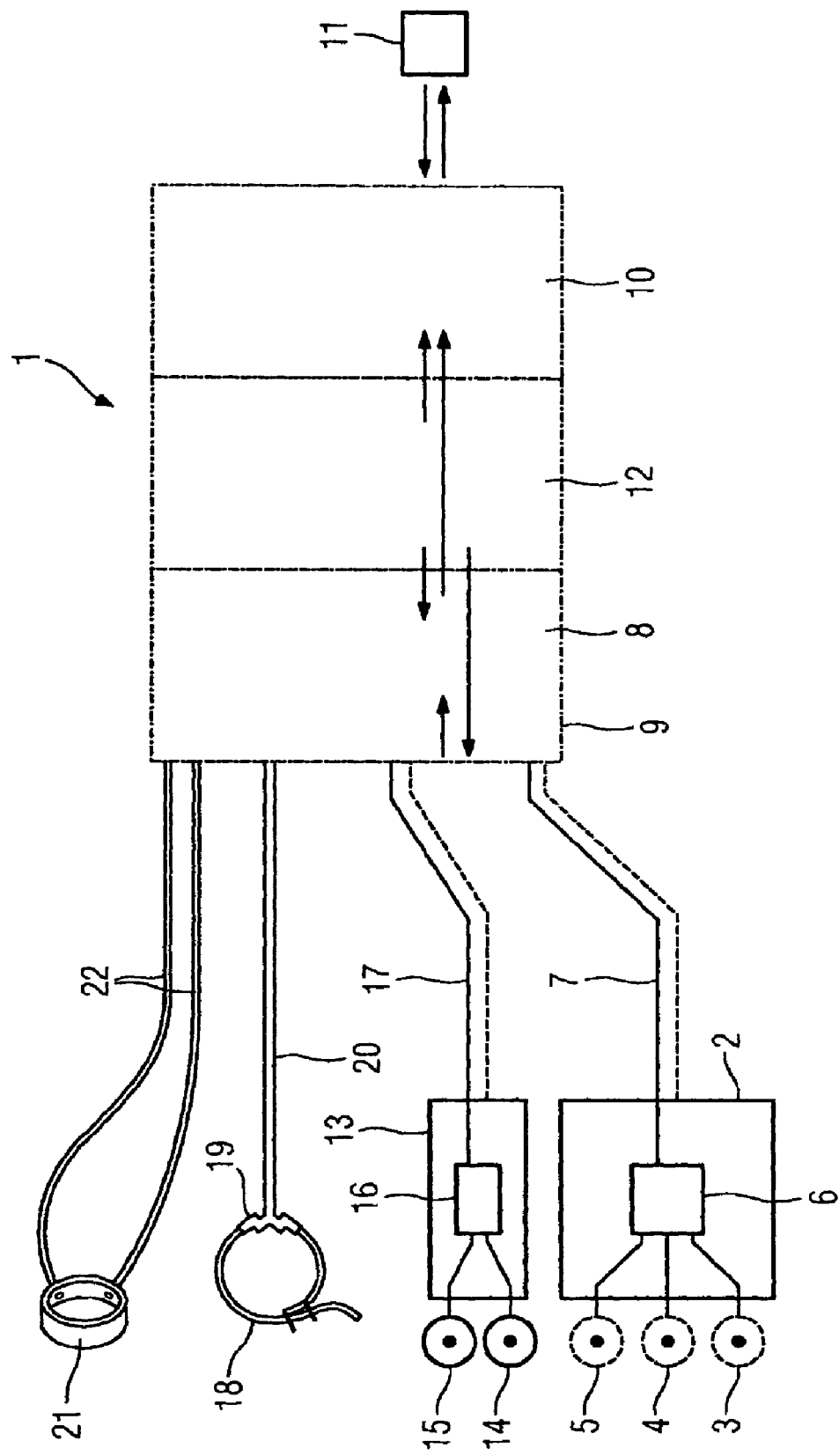
FIG. 1 shows a schematic diagram of a sensor system according to the prior art.

FIG. 1 shows an example of a physiological sensor system 1 according to the prior art in the form of a schematic diagram. The sensor system comprises a first shielded housing 2, to be arranged in close proximity to a patient, on which in the example illustrated are arranged three electrodes 3, 4 and 5 which are designed for example for recording an ECG. In the first housing 2 furthermore is arranged a signal amplifier unit 6 which amplifies the signals delivered by way of the electrodes 3, 4, 5. By way of a shielded or twisted cable 7, the measurement signals are delivered to a signal conversion module 8 which is located in a second shielded housing 9. There the signals are converted and then delivered by way of a signal transfer module 10 to an external signal processing and/or control unit 11. The second housing 9 also accommodates a power supply unit 12 which supplies the entire sensor system with power.

As FIG. 1 also shows, a second first housing 13 is provided, on which in the example illustrated two electrodes 14, 15 are likewise arranged. These are designed for example for recording EEG measurement signals. It is naturally also possible to provide more than two electrodes. This first shielded housing 13 also accommodates a signal amplifier unit 16 which amplifies the signals locally, in other words directly at the place of measurement. By way of a shielded or twisted cable 17, these measurement signals are also delivered to the signal conversion module 8 and prepared accordingly.

In addition, connected to the second shielded housing 8 is a further sensor element 18 which in the sample embodiment illustrated is a flexible chest ring which can be used to record the breathing of the patient. This comprises a compressible air volume 19 which is compressed or extended when the thorax rises and falls. The changing pressure is delivered to a corresponding sensor in the signal conversion module 8 by way of a pneumatic connecting line 20. A second sensor element 21 in the form of a finger ring is connected to the second housing 9, by means of which the peripheral pulse of the patient can be measured by light absorption of the blood. The non-electrical measurement information recorded (even in the case of the information recorded by means of the sensor element 18 this is non-electrical measurement information) is delivered here by way of fiber-optic lines 22 to a corresponding sensor element in the signal conversion module 8.

Figure 2:
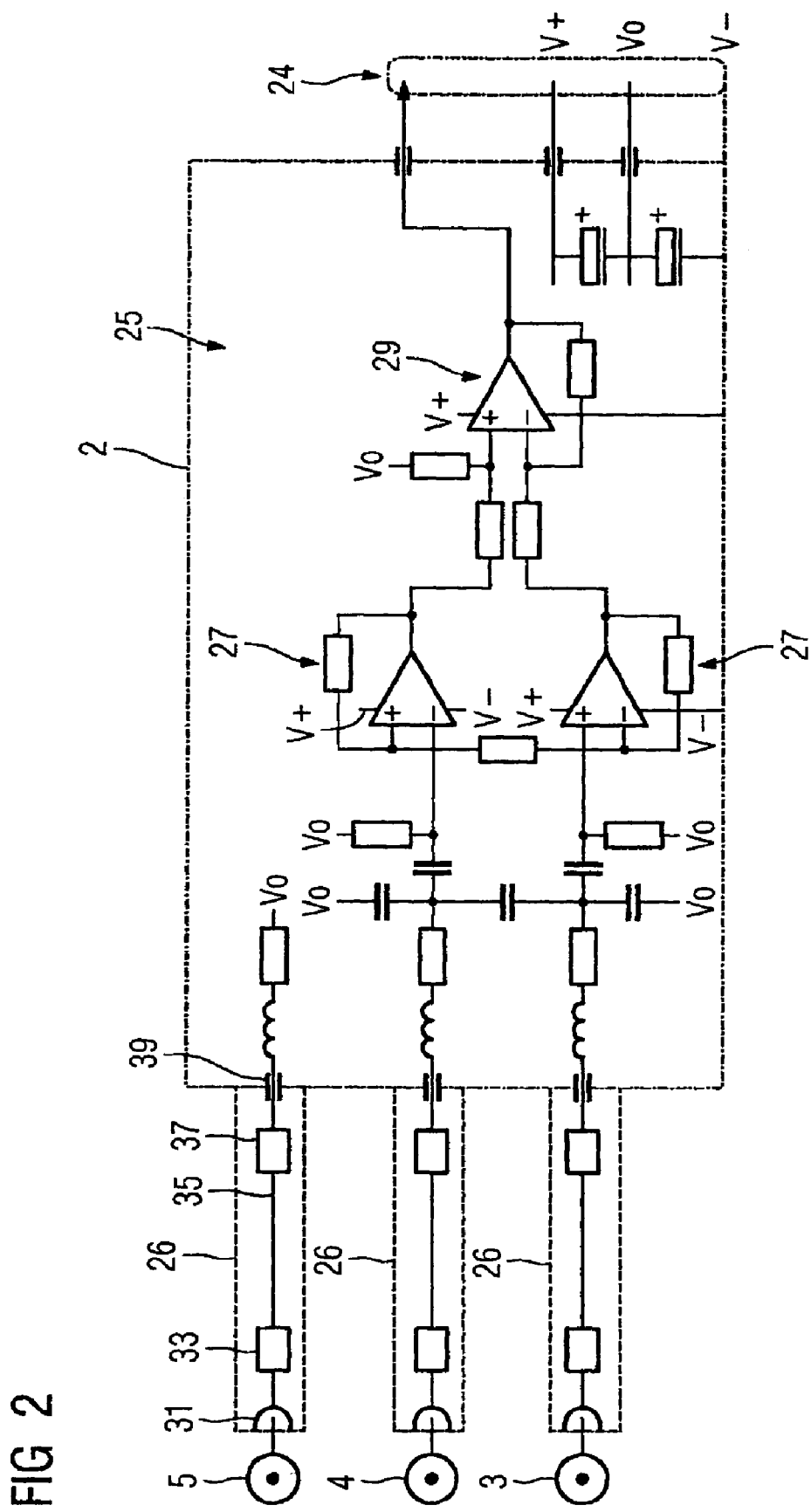
FIG. 2 shows an example of an embodiment of the signal amplifier unit.

FIG. 2 shows a diagrammatic sketch of the first housing 2 in an enlarged representation with a circuit arrangement 25. In the example illustrated, the electrodes 3, 4, 5 are shown connected to the housing 2 for mobility and also electrically by way of short cable connections 26. The ECG (or also the EEG) electrodes are stuck onto a patient who is not shown and are positioned according to the desired derivative of heart signals. The electrodes 3 and 4 are used for measurement signal recording, the electrode 5 is connected to ground and serves as a reference. Connected downstream of the electrodes 3 and 4 are two operational amplifiers 27 and also a common operational amplifier 29 for difference signal generation. Since only one signal is determined between the two electrodes 3, 4, only one signal output 24 is provided.

Alternatively, three derivatives are possible as a result of the orientation of the three electrodes 3, 4, 5, namely "left arm-right arm", "left leg-right arm" and "left leg-left arm". In contrast to the embodiment represented, these can be output in the form of a plurality of difference signals by way of a plurality of outputs 24. The output or transfer takes place by way of a shielded cable connection in each case.

The cable connections 26 each have at a first end a clip 31 which with the aid of a clamping zone permits clamping to the respective measuring electrode 3, 4, 5. The clip establishes the electrical connection from the measuring electrode 3, 4, 5 to a first resistor 33 which is arranged in close proximity to the measuring electrode 3, 4, 5. The cable connection 26 preferably has a length which means that when the measuring electrode 3, 4, 5 is arranged in the vicinity of the center of an imaging area of the magnetic resonance device the signal amplifier unit 6 is located close to the edge zone of the imaging area. For example, the cable connection has a length of 10 cm to 20 cm. The electrical connection over this distance is made by way of a low-impedance conductor 35 whose first end is soldered to the resistor 33 and whose second end is soldered to a resistor 37. Downstream of the resistor 37 the connecting cable 26 is routed through a feedthrough capacitor 39 into the interior of the shielded housing 2. The feedthrough capacitor 39 effects an HF-wise connection of the feedthrough cable 26 with the housing 2 and thus also to the other cable connections 26 with the other measuring electrodes 3, 4, 5. The feedthrough capacitor 39 is formed by the electrical conductor of the feedthrough cable and a tubular conductor located in the housing 2. In order to increase the capacitance the space between feedthrough cable and tubular conductor is filled with an insulating material with a high dielectric coefficient $\epsilon_r$. Feedthrough capacitors are also obtainable as discrete components of the leaded type or for surface mounting.

Such types of short cable connections are used for example in the case of a signal amplifier unit 6, 16. The central component of the cable connection 26 is the line made of sheathed copper braid which is provided with series resistances of 47 kOhm at both ends of the line. With the specified line lengths there is no longer any danger of burning. The series resistors are preferably integrated on the clip and the amplifier electronics. The resistance value can be adapted according to the line length.

Figure 3:
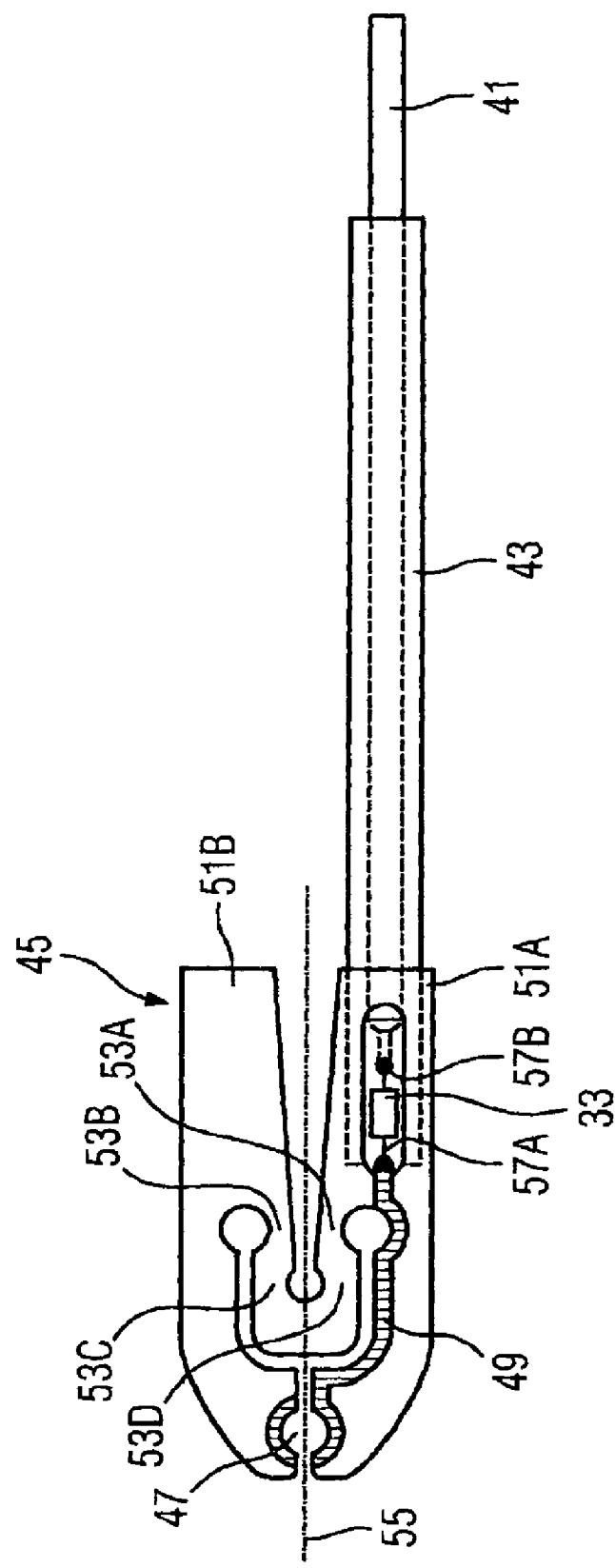
FIGS. 3 and 4 show representations of an electroplated clip for a measuring electrode.
Figure 4:
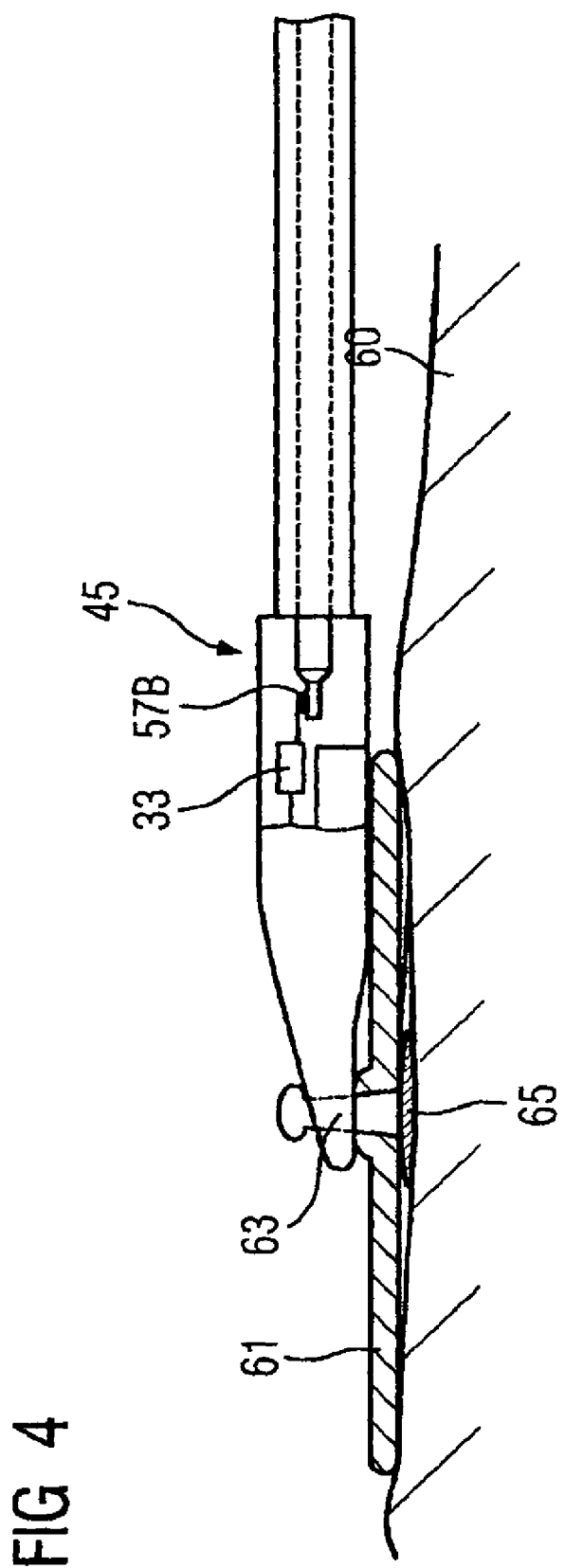

FIGS. 3 and 4 show a top view and a side view of a clip for use with a conventional single-use adhesive electrode. In FIG. 3 can be seen a low-impedance conductor 41 which is enclosed by an insulating tube 43. The pincer-like clip 45 is formed from thermally stable plastic. It has a clamping zone 47 into which a contact pin of the measuring electrode is to be clamped in order to connect it electrically to the conductor 41. Electrical contact is made by way of an electroplated area 49 which is shown hatched in FIG. 3. This leads to a grip section 51A of the clip 45, into which the conductor 41 is brought. The grip section 51A has a recess for the first resistor 33 which is soldered on the one hand to the conductor 41 and on the other hand to the electroplated area 49. The clip 45 has four bend zones 53A, . . . 53D which are arranged in meander fashion and symmetrically with respect to the direction of the spring force. The spring force on pressing together the grip sections 51A, 51B in the clamping zone 47 acts perpendicular to the axis of symmetry 55 in the drawing plane. The soldering points 57A, 57B bring about a good large area of contact between the conductor 41 and the measuring electrode.

FIG. 4 shows a side view of the clip 45 from FIG. 3, whereby a measuring electrode 61 placed on the skin 60 of a patient is clamped in the clamping zone of the clip by its contact pin 63. In order to make clear the arrangement of the resistor 33, the outer area of the clamping part 51 has not been drawn in order that the arrangement of the resistor 33 in the clip at a distance from the patient can be recognized. The clip 45 tapers in a wedge shape in the area of the clamping zone in order to facilitate the clamping of the measuring electrode 61. A cellular material impregnated with Ag/AgCl or an Ag/AgCl gel mass improves the electrical contact between measuring electrode 61 and skin 60 and results in the resistance of approximately 10 kΩ mentioned in the introduction.

The invention claimed is:
1. A physiological sensor system for recording an electrical measurement signal of a patient in a magnetic resonance device, comprising:
a first measuring electrode that measures a first electrical measurement signal of the patient;
a first signal amplifier unit connected to the first measuring electrode by a first cable connection and placed in a close proximity to the patient, wherein the first cable connection comprises:
a low-impedance conductor, a first electrical resistor connected with the first measuring electrode and arranged at a first end of the low-impedance conductor, and
a second electrical resistor connected with the first signal amplifier unit and arranged at a second end of the low-impedance conductor,
wherein the first and the second electrical resistor has a resistance value in an order of magnitude of an electrical resistance between a skin of the patient and the first measuring electrode;
a second measuring electrode that measures a second electrical measurement signal of the patient;
a second signal amplifier unit connected to the second measuring electrode by a second cable connection and placed in a close proximity to the patient, wherein the second cable connection comprises:
a low-impedance conductor,
a first electrical resistor connected with the second measuring electrode and arranged at a first end of the low-impedance conductor, and
a second electrical resistor connected with the second signal amplifier unit and arranged at a second end of the low-impedance conductor,
wherein the first and the second electrical resistor has a resistance value in an order of magnitude of an electrical resistance between a skin of the patient and the second measuring electrode;
a shielded housing in which the first and the second signal amplifier units are arranged, wherein the respective second end of the low-impedance conductor of the first and second cable connections is capacitively coupled to the shielded housing through a respective feedthrough capacitor, wherein the first and the second cable connections due to being capacitively coupled to the shielded housing form a shielded connection arrangement with respect to high-frequency signals resulting from operation of the magnetic resonance device;
a differential amplifier coupled to the first and second signal amplifier units to receive a respective output signal from the first and second signal amplifier units and supply a difference measurement signal; and
a signal processing unit connected to the differential amplifier to process the difference measurement signal.

2. The physiological sensor system as claimed in claim 1, wherein the first electrical resistor is soldered to the first end of the low-impedance conductor.

3. The physiological sensor system as claimed in claim 1, wherein the second electrical resistor is soldered to the second end of the low-impedance conductor.

4. The physiological sensor system as claimed in claim 1, wherein a length of the first and second cable connections is determined so that the first and second signal amplifier units is located close to an edge zone of the imaging area when the first and second measuring electrodes are arranged in a vicinity of a center of an imaging area of the magnetic resonance device.

5. The physiological sensor system as claimed in claim 1, wherein the length of the cable connections is in a range of 10 cm to 20 cm.

6. The physiological sensor system as claimed in claim 1, wherein the low-impedance conductor is a sheathed copper braid.

7. The physiological sensor system as claimed in claim 1, wherein each cable connection connects its measuring electrode by a respective clip that has a recess in which the first electrical resistor is located.

8. The physiological sensor system as claimed in claim 7, wherein the first electrical resistor connects the measuring electrode by a tin-plating of a clamping zone of the clip.

9. The physiological sensor system as claimed in claim 8, wherein a spring force of the clip is performed by four bend zones.

10. The physiological sensor system as claimed in claim 9, wherein the four bend zones are arranged symmetrically with respect to a direction of the spring force.

11. The physiological sensor system as claimed in claim 8, wherein one end of the first electrical resistor is soldered to the tin-plating of the clamping zone of the clip.

12. The physiological sensor system as claimed in claim 11, wherein another end of the first electrical resistor is soldered to the first end of the low-impedance conductor.

13. A method for recording an electrical measurement signal of a patient in a magnetic resonance device, comprising:
measuring a first electrical measurement signal of the patient by a first measuring electrode;
connecting the first measuring electrode to a first signal amplifier unit by a first cable connection comprising:
a low-impedance conductor,
a first electrical resistor connected with the first measuring electrode and arranged at a first end of the low-impedance conductor, and
a second electrical resistor connected with the first signal amplifier unit and arranged at a second end of the low-impedance conductor,
wherein the first and the second electrical resistor has a resistance value in an order of magnitude of an electrical resistance between a skin of the patient and the measuring electrode;
measuring a second electrical measurement signal of the patient by a second measuring electrode;
connecting the second measuring electrode to a second signal amplifier unit by a second cable connection comprising:
a low-impedance conductor,
a first electrical resistor connected with the second measuring electrode and arranged at a first end of the low-impedance conductor, and
a second electrical resistor connected with the second signal amplifier unit and arranged at a second end of the low-impedance conductor,
wherein the first and the second electrical resistor has a resistance value in an order of magnitude of an electrical resistance between a skin of the patient and the measuring electrode;
arranging in a shielded housing the first and the signal amplifier units;
capacitively coupling to the shielded housing each respective second end of the low-impedance conductor of the first and second cable connections through a respective feedthrough capacitor, wherein the first and the second cable connections by way of said capacitive coupling forming a shielded connection arrangement with respect to high-frequency signals resulting from operation of the magnetic resonance device;
coupling a differential amplifier to the first and second signal amplifier units to receive a respective output signal from the first and second signal amplifier units and supply a difference measurement signal; and
connecting the differential amplifier to a signal processing unit to process the difference measurement signal.

* * * * *